United States Patent [19]
Cassford

[11] Patent Number: 5,385,534
[45] Date of Patent: Jan. 31, 1995

[54] SPLINT ASSEMBLED FROM A FLAT STACKABLE KIT

[75] Inventor: Keith L. Cassford, Long Beach, Calif.

[73] Assignee: Smith & Nephew Donjoy Inc., Carlsbad, Calif.

[21] Appl. No.: 89,015

[22] Filed: Jul. 9, 1993

[51] Int. Cl.$^6$ .............................................. A61F 5/00
[52] U.S. Cl. .................................... 602/15; 602/5; 602/23
[58] Field of Search .................. 602/5, 6, 12, 15, 20, 602/23, 26; 128/870, 877, 878, 882

[56] References Cited

U.S. PATENT DOCUMENTS

| | | |
|---|---|---|
| 2,409,195 | 10/1943 | Crawford . |
| 3,496,934 | 2/1970 | Anderson . |
| 3,624,745 | 11/1971 | Bowers . |
| 3,653,378 | 4/1972 | Reuther . |
| 3,695,258 | 10/1972 | Castle . |
| 3,850,167 | 11/1974 | Seeley . |
| 3,853,123 | 12/1974 | Moore . |
| 3,896,799 | 7/1975 | Seeley . |
| 4,041,940 | 8/1977 | Frankel et al. . |
| 4,111,194 | 9/1978 | Cox et al. . |
| 4,209,011 | 6/1980 | Peck et al. . |
| 4,383,526 | 5/1983 | Robins . |
| 4,520,806 | 5/1985 | Miller . |
| 5,024,216 | 6/1991 | Shiono . |
| 5,195,944 | 3/1993 | Schlogel . |

Primary Examiner—Richard J. Apley
Assistant Examiner—Linda C. M. Dvorak
Attorney, Agent, or Firm—Rodney F. Brown

[57] ABSTRACT

A splint and a kit from which the splint is assembled include a plurality of components having a planar configuration for compact storage when in the kit, but having a three-dimensional configuration conforming to the desired body contours when the splint is assembled. The individual planar kit components include a rigid support member, a pad for cushioning the support member against the body, a plurality of straps for securing the support member to the body, and a pair of flexion members for fixedly retaining the flexion angle of the support member. The support member is an elongated surface having two longitudinal grooves formed therein that act as contour joints, and two slits formed therethrough perpendicular to the grooves that act as flexion joints. The joints remain fully extended and flat in the kit, but when the splint is assembled from the kit, the contour joints are flexed to impart a u-shape to the support member conforming to the desired contour of the body. The flexion joints are likewise flexed to a selected flexion angle for the body joint and the flexion members are fastened to the support member surface across the slits to fix the flexion angle.

20 Claims, 3 Drawing Sheets

SPLINT ASSEMBLED FROM A FLAT STACKABLE KIT

TECHNICAL FIELD

The present invention relates generally to a splint for immobilizing a body part, particularly to a splint assembled from a kit, and more particularly to a splint assembled from a flat stackable kit.

BACKGROUND OF THE INVENTION

A splint is used primarily as a short-term means for immobilizing a body part following an injury thereto. Where the injury is minor, such as a slight joint sprain, requiring a relatively short treatment period, the splint can serve as the primary treatment means for the duration of the treatment period. Where the injury is more severe, however, such as a broken bone or a torn ligament, the splint usually serves as an immediate, but only temporary, treatment means until more long-term treatment of the injured body part can be administered, often in the form of a brace or cast. Temporary splints are commonly employed under emergency post-trauma conditions in locales remote from treatment facilities.

Whether the splint provides primary or temporary treatment, effective immobilization of the affected body part requires a close fit between the splint and the body part. Splints, however, are usually produced in only one or a few generalized sizes because of the disposable nature of splints and the difficulty in stocking a large range of splint sizes and individually sizing each user during emergency applications. Accordingly, splints are preferably designed to be at least somewhat adjustable to the specific size requirements of the user with the object of enhancing the fit of the splint.

Unfortunately, splints, which are rigid by necessity, do not readily adapt to the contours of the body, and particularly to the contours of limbs encompassing flexible joints that frequently require splinting. Therefore, prior art designs for splints and other joint immobilizing devices have balanced a trade-off between closeness of fit and degree of rigidity.

U.S. Pat. No. 3,853,123 teaches a knee brace formed from a resilient shell that wraps around the leg and knee joint to restrain flexion of the knee joint. The shell is maintained in place by a plurality of pliable straps drawn tight to encircle the leg and shell. Although the brace provides a snug fit with the leg, its resilient components do not always provide sufficient rigidity and corresponding immobility for post-trauma applications. In addition, the brace does not permit setting the knee joint at a flexion angle other than the angle defined by the relatively straight axis of the leg.

U.S. Pat. No. 4,041,940 teaches a knee immobilizer that has a rigid u-shaped shell conforming to the leg of the user and having a slight flexion angle built into the shell about the knee joint. Although the shell provides a relatively close fit with the leg, its three-dimensional configuration renders the device impractical for emergency field applications. The device is difficult to store or transport at remote trauma sites due to the excessive bulk of the configuration. Additionally, the device is limited to one flexion angle which may not always be optimum for the particular application.

U.S. Pat. No. 2,409,195 discloses a splint having longitudinal joints formed therein for conformance of the splint to the substantially cylindrical lateral contour of the patient. The splint is further provided with lateral joints to conform the splint to the somewhat bowed longitudinal contour of the patient. However, the joints diminish the effectiveness of the splint because the joints cannot be fixed, and accordingly are easily flexed with movement of the patient.

U.S. Pat. No. 3,653,758 discloses a splint having a flexion joint formed therein for conformance of the splint to a desired flexion angle of the knee joint. The flexion joint of the splint can be fixed at a selected flexion angle by tightening a plurality of bolts at the joint. This task, however, is cumbersome, particularly in emergency situations where even common tools may not be available.

Accordingly, it is an object of the present invention to overcome the problems set forth above with respect to prior art splints and joint immobilizers. In particular, it is an object of the present invention to achieve a high degree of immobilization for an injured body part by providing a splint that is substantially rigid, yet is close-fittingly adaptable to various body sizes.

It is another object of the present invention to provide a splint for a body joint that can be rapidly and fixedly set to a desired angle of joint flexion. It is a further object of the present invention to provide a splint for a body joint that can be readily assembled from a kit without any tools, wherein the kit is highly compact and stackable enabling practical storage and transportation of a relatively large splint inventory at remote trauma sites or treatment centers.

SUMMARY OF THE INVENTION

The present invention is a splint and a flat stackable kit from which the splint is assembled. The splint comprises a support member for a body part, typically an arm or a leg. The support member is an elongated surface fabricated from a substantially rigid material. Two spaced-apart grooves are formed longitudinally in the surface of the support member. The grooves act as contour joints about which the support member is pivoted to selected contour angles, thereby providing the support member surface with a longitudinally aligned u-shape that substantially conforms to the contour of the splinted body part.

The support member also has two slits formed therethrough substantially perpendicular to each respective groove. Each slit extends from an opposing longitudinal edge of the support member to a respective groove in the support member surface. The slits are positioned on the splinted body part in correspondence with a body joint thereof, such as a knee or an elbow joint. The slits act as flexion joints about which the support member is pivoted to a selected flexion angle. Accordingly, the support member provides a support platform for the body joint at the selected flexion angle.

A rigid flexion member is further provided in association with each slit. Each flexion member has a planar surface sized to extend across the respective slit. The flexion member is fastened to the surface of the support member on each side of the slit with the slit pivotally separated in correspondence to the desired flexion angle. An adhesive is provided on the support member or flexion members to enable fastening of the support and flexion members together. The fastened flexion and support members accordingly maintain the desired flexion angle of the support member substantially fixed.

The splint further comprises a flexible foam pad positioned on the support member surface between the support member and the splinted body part to enhance the comfort of the user and to ensure the fit of the splint around the body part. The pad has a planar construction with slits formed therethrough corresponding to the slits through the support member. The pad slits enable flexion of the pad in correspondence to flexion of the support member. The splint is secured to the body by a plurality of flexible straps threaded through a plurality of loops integral with the support member, thereby enclosing the splint around the body part.

The above-described splint is assembled from a flat stackable kit comprising the support member, flexion members, adhesive fastener, pad and straps. While stored as a kit, the contour and flexion joints of the support member are maintained fully extended providing the support member with a planar configuration. The pad is likewise maintained in a planar configuration for compact storage of multiple kits stacked atop one another. The adhesive fastener on the support member or flexion members is covered with a removable nonadhesive shield to facilitate storage of the kit. The shield prevents accidental adhesion of the kit components together during storage until the kit is assembled as a splint.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

ASSEMBLED SPLINT

Figure 1:
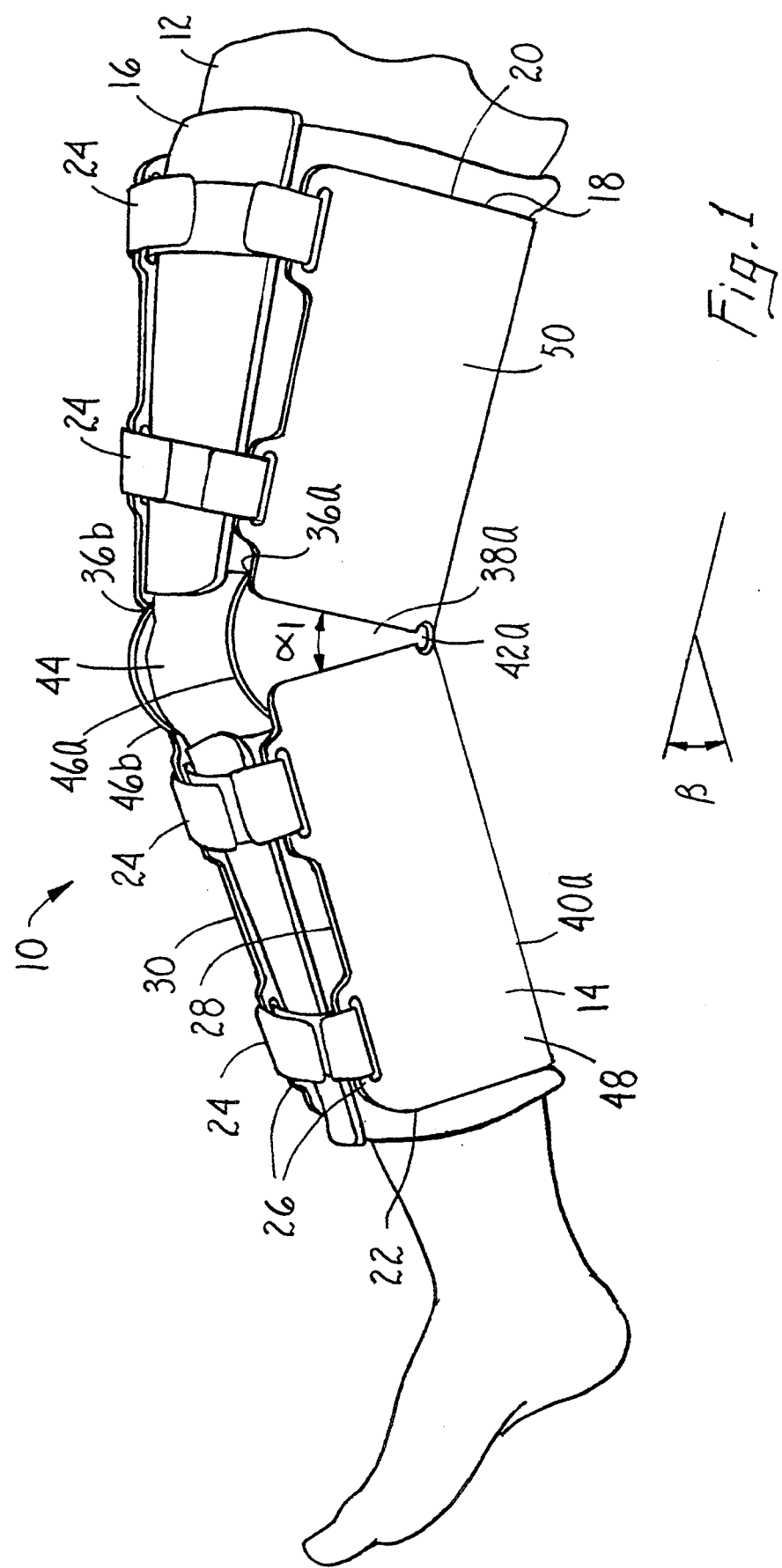
FIG. 1 is a perspective view of a splint of the present invention positioned in place on the leg of a user.

Referring initially to FIG. 1, an assembled splint of the present invention is shown and generally designated 10. The particular splint 10 described by way of example is a leg splint fitted to the leg 12 of a user. It will be apparent to one skilled in the art, however, that the splint 10 of the present invention can alternatively be applied to other body parts, and in particular to other body parts encompassing a flexible body joint, such as an arm encompassing an elbow, without substantial modification in accordance with the instant teaching.

The splint 10 comprises a support member 14 partially enclosing the leg 12. The support member 14 is fabricated from a sheet of a disposable lightweight material that is substantially rigid at the full thickness of the sheet, yet has a degree of flexibility at lesser thicknesses. The support member 14 can be cut in a single unitary piece from the desired sheet of material. Materials satisfying these criteria at a full thickness on the order of about $\frac{1}{8}$ inch or more include certain metals and hard plastics, such as polyethylene and others well known to the skilled artisan. The support member 14 has an elongated configuration preferably at least somewhat shorter than the leg 12 being splinted and is longitudinally bent about a pair of contour joints into a u-shape to approximate the underside contour of the leg 12 in a manner described hereafter.

A flexible compressible pad 16 is positioned between the leg 12 and the support member 14 on the inner side 18 of the support member surface to provide cushioning of the leg 12 against the rigid support member 14 as well as to provide a closer fit of the support member 14 to the underside of the leg 12. The pad 16 is fastened to the inner side 18 by a conventional adhesive such as glue. The pad 16 is preferably formed from a sheet of an inexpensive lightweight synthetic foam having a thickness on the order of about $\frac{1}{4}$ inch or more. The pad 16 can be cut in a single unitary piece from the desired sheet of material. The pad 16 is similarly configured to the support member 14, yet somewhat larger to overhang the relatively sharp edges of the support member 14 and provide cushioning between the leg 12 and the edges, particularly the end edges 20, 22. The pad 16 is also sufficiently large to wrap around and enclose the topside contour of the leg 12.

A plurality of substantially identical compliant straps 24 are threaded through strap loops 26 formed integrally with the opposing longitudinal edges 28, 30 of the support member 14. The straps 24 are preferably formed from a synthetic cloth and each is provided with a hook 32 and loop 34 fastener (shown in FIG. 2) enabling each strap 24 to be adjustably fastened onto itself, thereby forming a close-fitting removable circumferential enclosure of the leg 12 in cooperation with the support member 14 and pad 16. The pad 16 further functions to cushion the topside of the leg 12 from the straps 24 and to enable a closer fit of the straps around the topside of the leg 12.

A pair of flexion joints 36a and 36b are provided adjacent and substantially perpendicular to opposing longitudinal edges 28, 30, respectively. The flexion joint 36a shown in FIG. 1 comprises a slit 38a passing through the support member 14 and extending from the longitudinal edge 28 to a contour joint 40a. The flexion joint 36a further comprises a curved expansion aperture 42a formed through the support member 14 at the junction of the slit 38a and the contour joint 40a. The flexion joint 36b is substantially identical to the flexion joint 36a, having a corresponding slit 38b and expansion aperture 42b (shown in FIG. 3).

The splint 10 is positioned on the leg 12 such that the flexion joints 36a, 36b are adjacent to the knee joint 44, thus, enabling the knee joint 44 to assume a flexion angle $\beta$ defined by the flexion joints 36a, 36b. The flexion angle $\beta$ is the angle between the longitudinal axis of the lower section 48 of the splint and a straight line extending from the longitudinal axis of the upper section 50 of the splint. The flexion angle $\beta$ is set by simultaneously pivoting the flexion joint 36a a pivot angle $\alpha_1$ and pivoting the flexion joint 36b a pivot angle $\alpha_2$ (not shown). The angles $\alpha_1$ and $\alpha_2$ are the separation angles of slits 38a and 38b, respectively, preferably wherein $\alpha_1 = \alpha_2 = \beta$. The expansion apertures 42a, 42b reduce the stress on the support member 14 as the flexion joints 36a, 36b, respectively, are pivoted.

Flexion members 46a, 46b are provided in conjunction with the flexion joints 36a, 36b, respectively, to maintain the flexion angle $\beta$ in a fixed position. Accordingly, the flexion member 46a is fastened to the inner side 18 of the support member surface across the slit 38a and the flexion member 46b is correspondingly fastened to the inner side 18 of the support member surface across the slit 38b to effectively lock the flexion angle $\beta$. The flexion members 46a, 46b have a planar configuration fabricated from sheet material having substantially the same properties as the material forming the support member 14, the flexion members 46a, 46b and the support member 14 preferably being formed from an identical material. The flexion members 46a, 46b preferably have a semi-circular geometry to minimize sharpened corners on the exterior of the splint 10.

Figure 2:
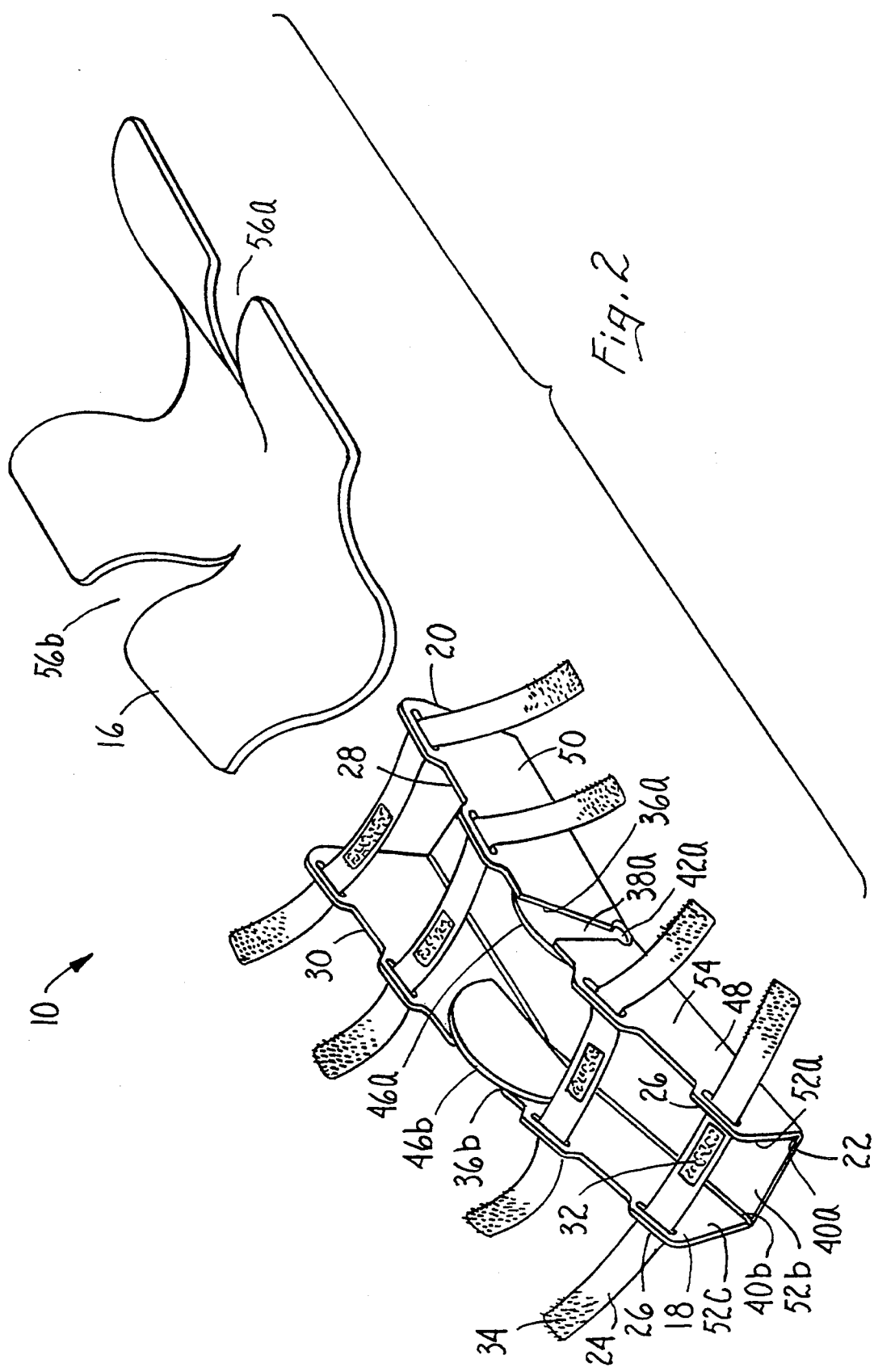
FIG. 2 is an exploded perspective view of the splint of FIG. 1.

Referring to FIG. 2, the contour joints 40a and 40b are shown to be longitudinal grooves formed in the inner side 18 of the support member surface. The contour joints 40a, 40b are formed by scoring the inner side 18 to partially, but not completely, penetrate through the support member 14. Accordingly, the support member 14 has a substantially reduced thickness at the contour joints 40a, 40b rendering them more flexible than the remainder of the support member 14 having a full thickness.

The contour joints 40a, 40b enable pivotal bending of the support member 14 thereat to form three contour faces 52a, 52b, 52c on the inner side 18 of the support member surface providing the u-shaped configuration of the support member 14. The contour joints 40a, 40b are preferably substantially inelastic and resistant to flexion such that the support member 14 maintains its u-shape after bending. It is apparent that the grooves functioning as the contour joints 40a, 40b can alternatively be formed in the outer side 54 of the support member surface opposite the inner side 18.

It is further noted with reference to FIG. 2 that the pad 16 has slits 56a, 56b formed therethrough corresponding to slits 38a, 38b of the support member 14. The slits 56a, 56b function in substantially the same manner as slits 38a, 38b to facilitate pivoting of the pad 16 about the knee joint 44 and further reduce bunching of the pad 16 between the body part and support member 14 when the splint is in place on the body.

KIT FOR SPLINT ASSEMBLY

The flat stackable kit, from which the above-described splint 10 is assembled, is shown and described with reference to FIG. 3, wherein the kit is generally designated 10'. The kit 10' is substantially identical to the splint 10 shown in FIGS. 1 and 2, except as described hereafter. Accordingly, elements of the kit 10' corresponding to elements of the splint 10 are referenced by corresponding primed numerals.

The kit 10' comprises a planar support member 14', a planar pad 16', straps 24', planar flexion members 46a', 46b', and adhesive fasteners 58. The support member 14' and pad 16' are maintained in a flattened condition with the flexion and contour joints 36a', 36b' and 40a', 40b' at full extension to facilitate storage of the kit 10'. It is noted that the contour joints 40a', 40b' converge in a slight taper to approximate the tapered shape of most splinted body parts.

The pad 16' is preferably preglued to the middle contour face 52b' of the support member 14', providing the kit 10' with a unitary planar laminate of the two components 14' and 16'. Despite the laminate construction, the pad 16' can, nevertheless, be folded away from the outer contour faces 52a', 52c' of the support member 14' to expose the flexion joints 36a', 36b', thereby permitting assembly of the kit 10'. Exposure of the flexion joints 36a', 36b', in particular, permits fastening of flexion members 46a', 46b' to the contour faces 52a', 52c', respectively, on the inner side 18' of the support member resulting in the assembled splint 10.

It is alternatively within the purview of the skilled artisan to fasten the flexion members 46a', 46b' to the support member 14' at a corresponding location on the outer surface 54' of the support member. This alternate construction obviates the need to fold back the pad 16' and expose the inner side 18' of the support member surface during assembly.

A pair of adhesive fasteners 58 is provided at each flexion joint 36a' and 36b'. One fastener 58 is positioned on either side of the respective slit 38a', 38b' for fastening of the respective flexion member 46a', 46b' thereto. A preferred fastener 58 is a contact adhesive, such as a segment of pressure sensitive tape shown in FIG. 3 having an exaggerated thickness for illustrative purposes.

The tape segment 58 is prefastened on one of its sides to the inner side 18' of the support member surface. The support member 14' having the tape segment 58 applied thereto is nevertheless freely stackable with the pad 16' and other components of the kit 10' without adhering thereto or without compromising the adhesive properties of the tape segment 58 because the exposed side of the tape segment 58 is protected from contact with the other splint components before assembly by a removable shield 60 of coated paper or a similar material positioned over the tape segment 58. It is understood that the fastener 58 can alternatively be prefastened to the flexion members 46a', 46b', rather than the support member 14', within the scope of the present invention.

The flexion members 46a', 46b' of the kit 10' are unfastened to the support member 14' enabling individualized setting of the flexion angle $\beta$ during assembly of the kit 10'. Accordingly, the planar flexion members 46a', 46b' are loosely stackable with the support member 14' and pad 16'.

Figure 3:
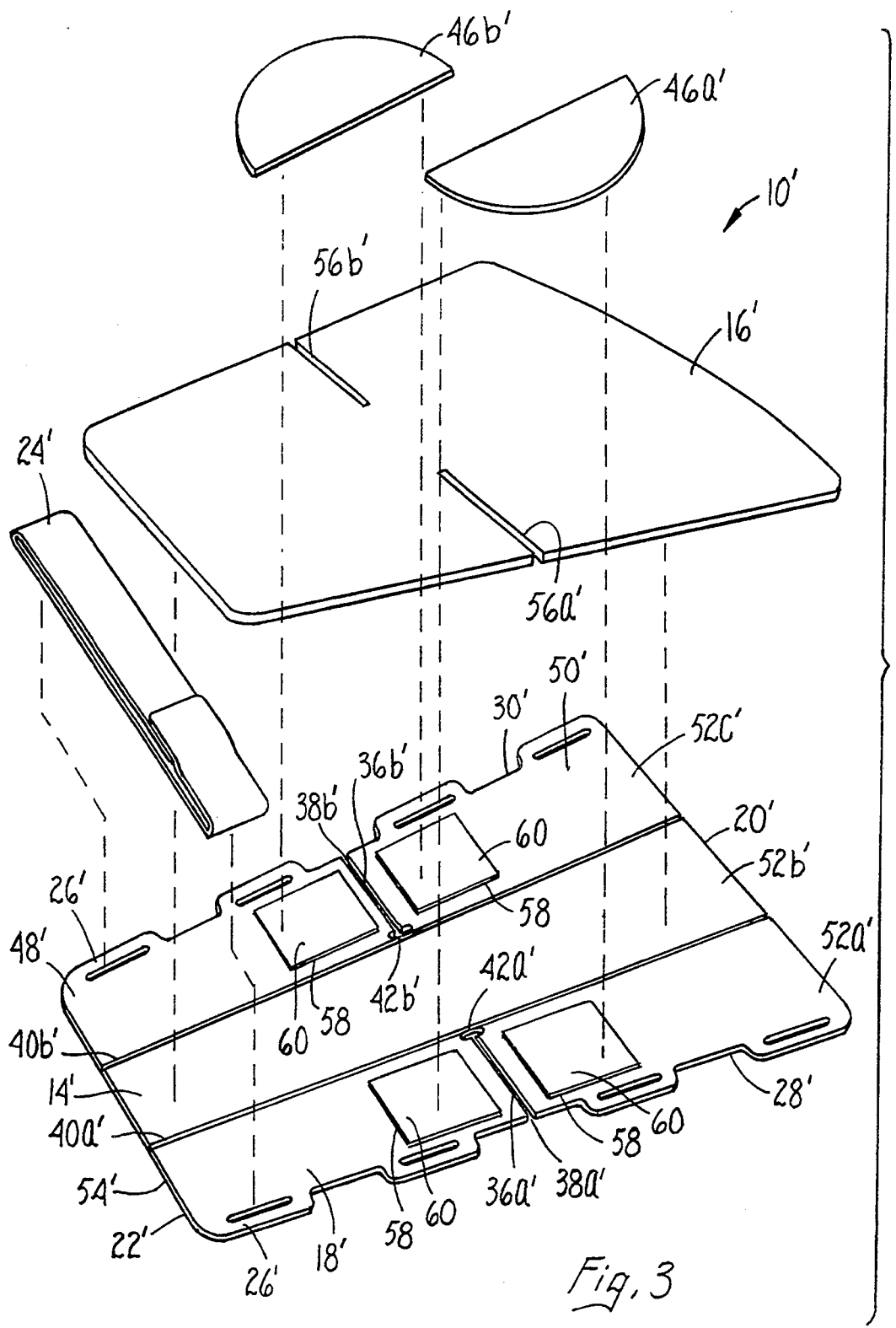
FIG. 3 is an exploded perspective view of a flat stackable kit from which the splint of FIG. 1 is assembled.

The straps 24' (only one strap is shown in FIG. 3 for clarity) are prethreaded through the strap loops 26' and folded enabling stackable storage of the substantially planar configured straps 24' with the remainder of the flat kit 10'. Alternatively, the straps 24' may be coiled for compactness in a manner not shown, but readily apparent to the skilled artisan, and stored separately from the remainder of the flat kit 10'.

METHOD OF KIT ASSEMBLY

The kit 10' is preferably assembled to create a splint 10 according to one of two embodiments. In a first embodiment, the flat support member 14' is initially shaped to the body part contour away from the body part, using the body part as a visual model, and the resulting splint 10 is subsequently positioned on the body part. In a second embodiment, the flat support member 14' of the kit 10' is initially positioned on the body part being splinted and subsequently shaped to the body part contour, using the body part as a direct form for the resulting splint 10.

In the first embodiment, assembly of the kit 10' is initiated by pivotally bending the contour joints 40a', 40b' to provide a substantially u-shaped configuration for the support member 14'. The desired flexion angle of the body joint on the body part being splinted is then determined, wherein the flexion angle of the body joint corresponds substantially identically with the flexion angle $\beta$ of the support member 14'. The desired flexion angle $\beta$ is formed in the support member 14' by pivotally separating slits 38a', 38b' about the expansion apertures 42a', 42b' to separation angles $\alpha_1$ and $\alpha_2$, respectively, such that $\alpha_1 = \alpha_2 = \beta$. The flexion angle $\beta$ is typically an acute angle ranging from about 0° to about 60° or less.

The flexion angle β of the support member 14' is fixed by folding back the pad 16' and removing the shields 60 from the tape segments 58. A flexion member 46a', 46b' is adhered to each pair of tape segments 58 across a separated slit 38a', 38b' at the respective flexion joint 36a', 36b'. Thereafter, the pad 16' is replaced over the joints 36a', 36b'. The prethreaded straps 24' are loosened in the loops 26', and the fully formed support member 14 as shown in FIG. 2 is slid onto the body part being splinted with the pad 16 positioned therebetween. Once the support member 14 is on the body part, the pad 16 is folded over itself between the body part and the straps 24. Finally, the straps 24 are tightened by cinching the straps 24 through the loops 26 and fastening the straps 24 onto themselves.

The second embodiment of assembling the kit 10' is substantially identical to the first embodiment, except that the flat support member 14' is placed on the body part being splinted before, rather than after, the flexion and contour joints 36a', 36b' and 40a', 40b' are adjusted. The joints, pad and straps are all positioned and function in substantially the same manner as described above once the support member 14' is in place on the body.

The assembled splint 10, as shown in FIG. 1, is designed to be retained on the leg 12 or other affected body part for several hours to several days as needed during the post-trauma period, thereby effectively immobilizing the body part. Thereafter, the splint 10, which is fabricated from inexpensive materials, can be readily disposed of.

While the forgoing preferred embodiments of the invention have been described and shown, it is understood that alternatives and modifications, such as those suggested and others, may be made thereto and fall within the scope of the invention.

I claim:

1. A flat stackable kit for a splint in a disassembled state comprising:
   a support member for a body part of a user being splinted, wherein said support member is formed from a substantially rigid material and has an elongated substantially planar surface with a first longitudinal edge bordering said support member surface and a second longitudinal edge bordering said support member surface opposite said first longitudinal edge;
   a contour joint formed substantially longitudinally in said support member surface and flattened in a fully extended position;
   a flexion joint formed substantially perpendicular to said contour joint in said support member surface and flattened in a fully extended position;
   a substantially rigid flexion member having a substantially planar surface and detached from said support member surface when said kit is in the disassembled state, while sized to be extendable across at least a portion of said flexion joint when said kit is assembled as the splint; and
   means for fastening said flexion member surface to said support member surface across said flexion joint when said kit is assembled as the splint.

2. A flat stackable kit for a splint as recited in claim 1 wherein said contour joint is a groove formed in said support member surface.

3. A flat stackable kit for a splint as recited in claim 1 wherein said contour joint is a first contour joint and further comprising a second contour joint, said second contour joint being a groove formed substantially longitudinally in said support member surface a distance apart from said first contour joint.

4. A flat stackable kit for a splint as recited in claim 1 wherein said flexion joint is a slit through said support member surface extending from a first end of said flexion joint at said first longitudinal edge of said support member surface across a portion of said support member surface to a second end of said flexion joint.

5. A flat stackable kit for a splint as recited in claim 4 further comprising an expansion aperture at said second end of said flexion joint.

6. A flat stackable kit for a splint as recited in claim 1 wherein said flexion joint is a first flexion joint and further comprising a second flexion joint, said second flexion joint including a slit formed substantially perpendicular to said contour joint and extending from a first end of said second flexion joint at said second longitudinal edge of said support member surface through a portion of said support member surface to a second end of said second flexion joint.

7. A flat stackable kit for a splint as recited in claim 1 further comprising a substantially planar flexible pad positionable on said support member surface.

8. A flat stackable kit for a splint as recited in claim 1 further comprising means for securing said support member to the body part being splinted.

9. A flat stackable kit for a splint as recited in claim 1 wherein said fastening means is an adhesive positioned on said support member surface or on said flexion member surface.

10. A splint comprising:
    a support member for a body part wherein said support member is formed from a substantially rigid material and has an elongated surface with a first longitudinal edge bordering said support member surface and a second longitudinal edge bordering said support member surface opposite said first longitudinal edge;
    a contour joint formed substantially longitudinally in said support member surface, said support member surface pivoted about said contour joint at a contour angle;
    a flexion joint formed substantially perpendicular to said contour joint in said support member surface, said support member surface pivoted about said flexion joint at a flexion angle;
    a substantially rigid flexion member having a first end with a first flexion member surface and a second end with a second flexion member surface, wherein said first flexion member surface engages said support member at a first point of said support member surface and said second flexion member surface engages said support member at a second point on said support member surface positioned across said flexion joint from said first point; and
    means for fastening said first and second flexion member surfaces to said first and second points on said support member surface, respectively, thereby maintaining said flexion angle substantially fixed.

11. A splint as recited in claim 10 wherein said contour joint is a groove formed in said support member surface.

12. A splint as recited in claim 10 wherein said flexion joint is a slit through said support member surface extending from a first end of said flexion joint at said first edge of said support member surface across a portion of said support member surface to a second end of said flexion joint.

13. A splint as recited in claim 12 further comprising an expansion aperture at said second end of said flexion joint.

14. A splint as recited in claim 10 further comprising a flexible pad positioned on said support member surface.

15. A splint as recited in claim 10 wherein said fastening means is an adhesive positioned between said first and second points on said support member surface and said first and second flexion member surfaces, respectively.

16. A splint comprising:
a support member for a body part wherein said support member is formed from a substantially rigid material and has an elongated surface with a first side, a second side opposite said first side, a first longitudinal edge bordering said support member surface, and a second longitudinal edge bordering said support member surface opposite said first edge;
a first contour joint being a groove formed substantially longitudinally in said support member surface, said support member surface pivoted about said first contour joint at a first contour angle;
a second contour joint being a second groove formed substantially longitudinally in said support member surface a distance apart from said first contour joint, said support member surface pivoted about said second contour Joint at a second contour angle:
a first flexion joint being a first slit formed substantially perpendicular to said first contour joint through said support member and extending from a first end of said first flexion joint at said first longitudinal edge of said support member surface to a second end of said first flexion joint adjacent to said first contour joint, said support member surface pivoted about said first flexion joint at a first flexion angle;
a second flexion joint being a second slit formed substantially perpendicular to said second contour joint through said support member and extending from a first end of said second flexion joint at said second longitudinal edge of said support member surface to a second end of said second flexion joint adjacent to said second contour joint, said support member surface pivoted about said second flexion joint at a second flexion angle;
a substantially rigid flexion member having a first end with a first flexion member surface and a second end with a second flexion member surface, wherein said first flexion member surface engages said support member at a first point on said support member surface and said second flexion member surface engages said support member at a second point on said support member surface positioned across said first flexion joint from said first point; and
means for fastening said first and second flexion member surfaces to said first and second points on said support member surface, respectively, thereby maintaining said first flexion angle substantially fixed.

17. A splint as recited in claim 16 further comprising an expansion aperture at said second end of said first or second flexion joint.

18. A splint as recited in claim 16 wherein said flexion member is a first flexion member and further comprising a second substantially rigid flexion member having a third end with a third flexion member surface and a fourth end with a fourth flexion member surface, wherein said third flexion member surface engages said support member at a third point on said support member surface and said fourth flexion member surface engages said support member at a fourth point on said support member surface positioned across said second flexion joint from said third point.

19. A splint as recited in claim 16 wherein said first and second flexion angles are substantially equal.

20. A splint comprising:
a support member for a body part wherein said support member is formed from a substantially rigid material and has an elongated surface with a first longitudinal edge bordering said support member surface and a second longitudinal edge bordering said support member surface opposite said first longitudinal edge;
a contour joint formed substantially longitudinally in said support member surface, said support member surface pivoted about said contour joint at a contour angle;
a flexion joint formed substantially perpendicular to said contour joint in said support member surface, said support member surface pivoted about said flexion joint, thereby dividing said support member surface into an upper section having an upper longitudinal axis and a lower section having a lower longitudinal axis, wherein the downward rotation of said lower longitudinal axis away from said upper longitudinal axis defines a flexion angle $\beta$;
means for maintaining said flexion joint at said flexion angle $\beta$ having a non-negative value of at least zero degrees, wherein said maintaining means is a substantially rigid flexion member having a flexion member surface positioned across at least a portion of said flexion joint; and
means for fastening said flexion member surface to said support member surface, thereby maintaining said flexion angle $\beta$ substantially fixed.

* * * * *